United States Patent
Smeets et al.

(10) Patent No.: US 7,141,668 B2
(45) Date of Patent: Nov. 28, 2006

(54) PROCESS FOR RECOVERING CAPROLACTAM

(75) Inventors: Theodorus M Smeets, Elsloo (NL); Gerardus W. A. Hangx, Weert (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/495,862

(22) PCT Filed: Nov. 25, 2002

(86) PCT No.: PCT/NL02/00761

§ 371 (c)(1),
(2), (4) Date: Nov. 16, 2004

(87) PCT Pub. No.: WO03/045911

PCT Pub. Date: Jun. 5, 2003

(65) Prior Publication Data

US 2005/0176954 A1    Aug. 11, 2005

(30) Foreign Application Priority Data

Nov. 26, 2001  (NL) .................................. 1019432

(51) Int. Cl.
*C07D 201/16* (2006.01)
(52) U.S. Cl. ....................................................... 540/540
(58) Field of Classification Search .................. 540/540
See application file for complete search history.

(56) References Cited

U.S. PATENT DOCUMENTS

| | | | |
|---|---|---|---|
| 4,457,807 A | 7/1984 | Rulkens |
| 4,563,308 A | 1/1986 | Plantema |
| 4,882,430 A | 11/1989 | Neubauer |

*Primary Examiner*—Bruck Kifle
(74) *Attorney, Agent, or Firm*—Nixon & Vanderhye, P.C.

(57) ABSTRACT

The invention relates to a process for recovering caprolactam from a mixture comprising caprolactam, water, light and heavy components, by subjecting the mixture to a first vacuum distillation resulting in a first bottom product comprising heavy components and caprolactam and in a fist overhead product comprising caprolactam, water, unsaturated lactams and light components; and subjecting at least part of the unsaturated lactams to a hydrogenation.

11 Claims, 1 Drawing Sheet

PROCESS FOR RECOVERING CAPROLACTAM

CROSS REFERENCE TO RELATED APPLICATION

Figure 1:
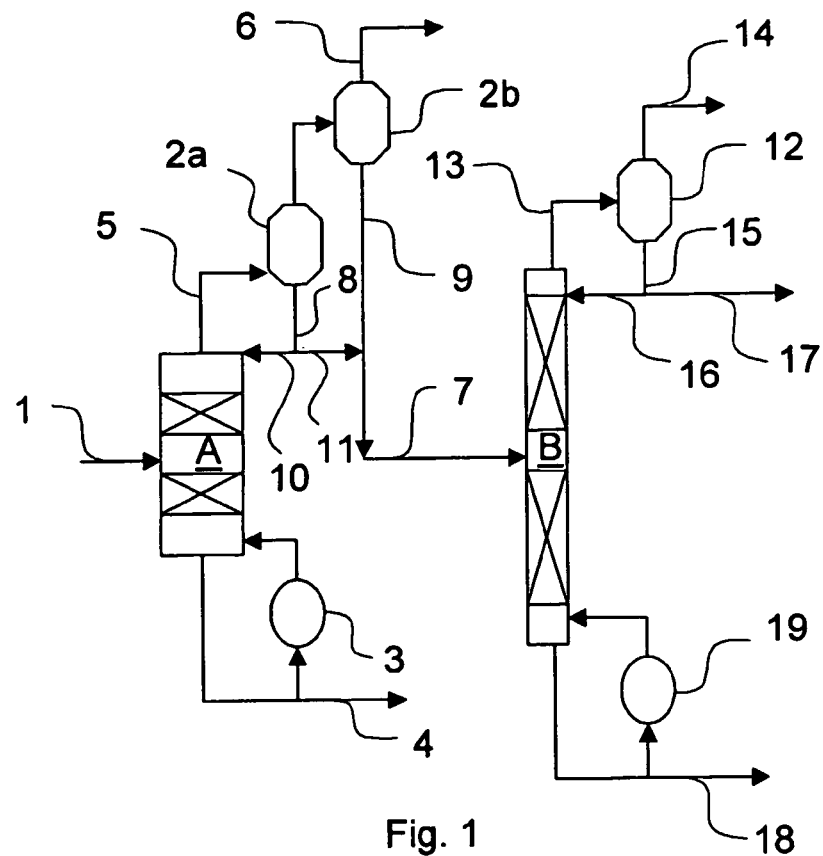

This application is the National Phase of International Application PCT/NL02/00761 filed Nov. 25, 2002 which designated the U.S., and was published in English.

The invention relates to a progress for recovering caprolactam from a mixture comprising caprolactum, water, light and heavy components.

Mixtures comprising caprolactam, water, heavy and light components from which caprolactam is to be recovered are generally encountered in processes for the preparation of caprolactam in which cyclohexanone oxime is converted into caprolactam with the aid of an acid, usually oleum. This conversion is known as the Beckmann rearrangement. A base, preferably ammonia, may be added to the Beckmann rearrangement mixture, resulting in a neutralized Beckmann rearrangement mixture. During the Beckmann rearrangement and the subsequent neutralization by-products are formed that are present as harmful components in an aqueous caprolactam stream. These components may adversely affect the quality of the caprolactam and the polymerization product prepared from it. Depending on the fact whether boiling points of components, under distillation conditions, are higher or lower than the boiling point of caprolactam they will hereafter be referred to as heavy or light components, respectively. It is desirable to remove these components, just like the water, from the caprolactam. This can be effected by one or more physical and/or chemical operations following the neutralisation. These operations may include, usually in combination, among other things: extraction, distillation, crystallization, ion exchange, oxidation, evaporation and hydrogenation.

EP-A-0 065168 describes a process for recovering caprolactam from a mixture comprising caprolactam, water, heavy and light components. In said process a caprolactam of 95–99.9% purity is fed to a first vacuum-operated distillation column, with the separation being controlled so that light components are discharged, as distillate (first top product), over the top of the column, while a bottom product consisting of caprolactam and the heavy components is fed to a second vacuum-operated distillation column. In the second column a separation is effected between caprolactam and the heavy components.

It has been found that light components with boiling points that under distillation conditions do not differ much from the boiling point of caprolactam, can also be present in such mixture comprising caprolactam, water, lights and heavy components and that such light components are difficult to remove. This concerns in particular the so-called unsaturated lactams (USL).

On the formula sheet, four of such unsaturated lactams with their structural formulae are drawn and denoted as USL-1, USL-2, USL-3 and USL-4.

The quality of caprolactam can be indicated by means of, among other things, the so-called PAN number, which is determined according to ISO standard 8660. The PAN number is a measure of the oxidizable impurities content in caprolactam. The USL's inter alia belong to the oxidizable impurities. The lower this number, the fewer oxidizable impurities.

The aim of the invention is to provide an efficient process for separating caprolactam from unsaturated lactams.

The process according to the invention allows effective separation of unsaturated lactams with no or substantially no loss of caprolactam.

This aim is achieved by subjecting the mixture to a first vacuum distillation resulting in a first bottom product comprising heavy components and caprolactam and in a first overhead product comprising caprolactam, water, unsaturated lactams and light components (other than unsaturated lactams); and subjecting at least part of the unsaturated lactams to a hydrogenation.

The process of the present invention allows the first vacuum distillation to be carried out such that the amount of unsaturated lactams in the first bottom product is at most 9 parts per million, preferably at most 6 parts per million, more preferably at most 3 parts per million (relative to the amount of caprolactam in the first bottom product), without resulting in substantial loss of caprolactam. Any suitable distillation conditions can be applied to obtain a first bottom product having an amount of unsaturated lactams of at most 9 parts per million, preferably at most 6 parts per million, more preferably at most 3 parts per million (relative to the amount of caprolactam in the first bottom product). The term parts per million is understood to mean the ratio consisting of grams of the specified substance per one million grams of caprolactam in a mixture comprising the specified substance and caprolactam. Preferably, this is achieved by carrying out the distillation such that the first overhead product contains caprolactam, the amount of caprolactam in the first overhead product preferably being higher than 0.1%, more preferably higher than 0.2% and even more preferably higher than 0.5% relative to the amount of caprolactam in the mixture fed to the first vacuum distillation. The first vacuum distillation is preferably performed in a vacuum distillation column (hereinafter referred to as first vacuum distillation column). Preferably, the applied pressure at the top of the first vacuum distillation column is between 0.2 and 5 kPa and the bottom temperature is between 90 and 170° C.

At least part of the unsaturated lactams are subjected to a hydrogenation resulting in that unsaturated lactams are converted into caprolactam. Hydrogenation has the additional advantage that unsaturated lactams are converted into valuable caprolactam which results in a further improvement in efficiency. In addition, hydrogenation of a mixture of caprolactam and unsaturated lactams renders the separation of unsaturated lactams from such mixture superfluous without these unsaturated lactams retaining their harmful properties. Hydrogenation may be effected in any suitable way which involves reacting of unsaturated components, for example unsaturated lactams with hydrogen. The hydrogenation may be performed in the presence of a hydrogenation catalyst known per se. Preferably, the hydrogenation is performed in the presence of a heterogeneous hydrogenation catalyst. Examples of such hydrogenation catalysts are ruthenium on aluminium oxide, rhodium on aluminium oxide, platinum on carbon, palladium on carbon, Raney nickel, nickel on silica and nickel on aluminium oxide. Preferably use is made of nickel-containing catalysts. The hydrogenation may for instance take place in a stirred tank reactor in which the catalyst particles are suspended in the mixture to be hydrogenated. Preferably, the hydrogenation is effected in a fixed-bed reactor with the catalyst being fixed in the reactor. The hydrogenation temperature is generally between 20 and 160° C. As a rule a not too low temperature will be chosen, for at a low temperature the reaction time is longer. The temperature is as a rule not too high because high temperatures have a negative influence on the caprolactam quality. The temperature therefore preferably is between 100 and 130° C. The hydrogenation pressure may be between 0.1 and 15 MPa. Preferably the pressure is between 0.3 and 5 MPa. The amount of hydrogen used will inter alia depend on the pressure, temperature and solubility of hydrogen and the amount of unsaturated lactams to be hydrogenated. The hydrogenation can advantageously be carried out as for example described in EP-A-635487.

The mixture of caprolactam, water, light and heavy components which is subjected to the first vacuum distillation preferably contains more than 99 wt. % caprolactam, more preferably contains more than 99.9 wt. % caprolactam.

If a hydrogenation reactor is already present upstream of the first vacuum distillation (seen in the direction of the flow of the mixture) in the process for recovering and purifiying caprolactam from a neutralized Beckmann rearrangement mixture, hydrogenation of at least part of the unsaturated lactams is preferably effected in this hydrogenation reactor.

In the process of the invention, the mixture comprising caprolactam, water, light and heavy components is preferably subjected to a hydrogenation in a hydrogenation reactor prior to the first vacuum distillation. More preferably, hydrogenation of at least part of the unsaturated lactams is effected in said hydrogenation reactor.

The process of the invention preferably comprises separating the first overhead product into a first part containing water and light components (of which at least the larger part are light components other than unsaturated lactams) and a second part containing caprolactam and unsaturated lactams; and hydrogenating said second part resulting in a hydrogenated mixture. The process preferably further comprises recovering caprolactam from said hydrogenated mixture. From a practical point of view, said hydrogenated mixture is preferably recycled to the first vacuum distillation of the process of the invention. It is to be understood that recycling the hydrogenated mixture to the first vacuum distillation may also include subjecting the hydrogenated mixture to one or more further steps prior to such recycling. Preferably the second part is recycled to the hydrogenation reactor in which the mixture comprising caprolactam, water, light and heavy components is preferably hydrogenated before it is preferably fed to the first vacuum distillation. It is to be understood that recycling the second part to said hydrogenation reactor may also include subjecting the second part to one or more further steps prior to such recycling to the hydrogenation reactor.

In one embodiment of the invention, the separating of the first overhead product into a first part containing water and light components and a second part containing caprolactam and unsaturated lactams is advantageously carried out by condensation of the first overhead product. In this embodiment of the invention, the first vacuum distillation is preferably carried out at an applied pressure at the top of the first vacuum distillation of between 1 and 5 kPa and a bottom temperature of between 120 and 170° C. This embodiment is especially advantageous when the amount of unsaturated lactams in the mixture fed to the first vacuum distillation is relatively low and/or when it is allowed that the amount of unsaturated lactams in the first bottom product is relatively high.

In a further embodiment of the invention, the second part may be a second bottom product, for instance obtained by subjecting the first overhead product to a second vacuum distillation resulting in a second overhead product comprising water and light components (of which at least the larger part are light components other than unsaturated lactams) and in a second bottom product comprising caprolactam and unsaturated lactams. In this further embodiment of the invention, said second bottom product is hydrogenated. In this further embodiment of the invention, the first vacuum distillation is preferably carried out at an applied pressure at the top of the first vacuum distillation column of between 0.2 and 3 kPa and a bottom temperature between 90 and 160° C. The second vacuum distillation is preferably performed in a vacuum distillation column (hereinafter referred to as second vacuum distillation column). Preferably, the second vacuum distillation is carried out such that the amount of caprolactam in the second overhead product is lower than 0.1%, more preferably lower than 0.01% relative to the amount of caprolactam in the first bottom product. The second vacuum distillation is preferably carried out at an applied pressure at the top of the second vacuum distillation column of between 1 and 5 kPa and a bottom temperature between 120 and 170° C. This further embodiment of the invention is especially advantageous when the amount of unsaturated lactams in the mixture fed to the first vacuum distillation is relatively high and/or when it is required that the amount of unsaturated lactams in the first bottom product is relatively low.

Before feeding the first overhead product comprising water, caprolactam, unsaturated lactams and other light components to the second vacuum distillation in the further embodiment of the invention, the first overhead product is advantageously separated by condensation in one or more condensation devices into a first part containing mainly water, which first part is preferably discharged to the vacuum, and a second part containing caprolactam and unsaturated lactams and other light components, which second part is subjected to the second vacuum distillation.

The second overhead product is advantageously separated by condensation into a fraction that contains mainly, for instance more than 80 wt. %, water and contains a part of the light components present in the mixture fed to the second vacuum distillation, which fraction is preferably discharged to the vacuum, and a fraction that contains the remainder of the light components present in the mixture fed to the second vacuum distillation, which fraction can be used as reflux for the second vacuum distillation and/or it can be drained or incinerated.

The first bottom product preferably contains more than 90 wt. % of the caprolactam present in the mixture which is fed to the first vacuum distillation. The first bottom product containing heavy components and the larger part of the caprolactam is generally fed to a subsequent separation operation for the separation of caprolactam and heavy components. The first overhead product comprises the remainder of the caprolactam fed to the first vacuum distillation.

The invention will be explained below with reference to examples and a drawing, without any intention of limiting the invention to these.

Figure 2:
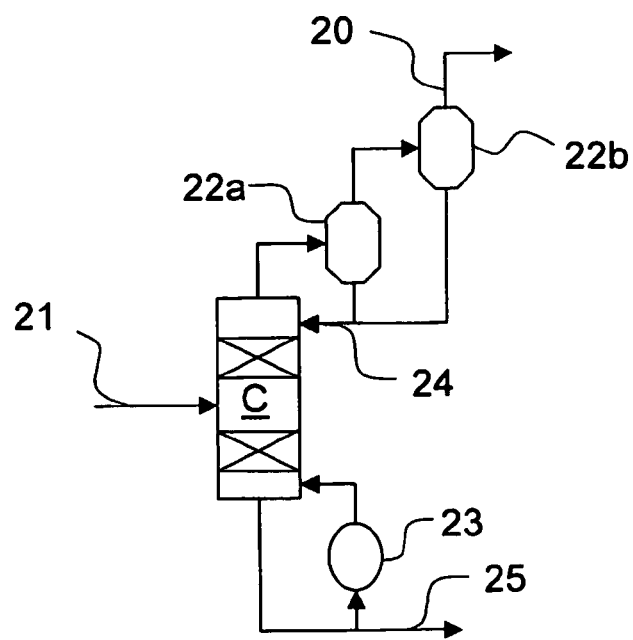
Figure 1:
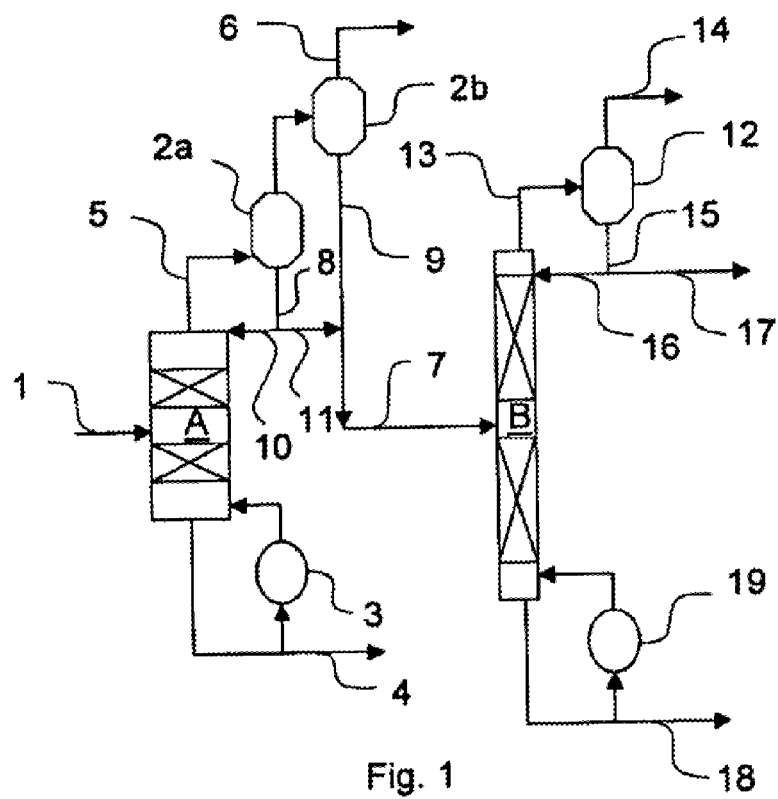
Figure 2:
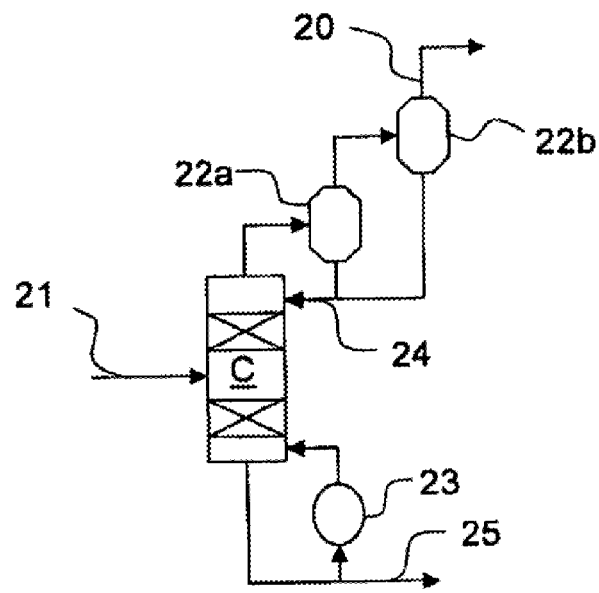

In the drawing FIG. 1 is the schematic representation of the practical example of the process according to the invention and FIG. 2 is the schematic representation of the comparative example.

EXAMPLE

Through line 1 passes the feed of a first vacuum distillation column A with a condensation device consisting of two stages 2a and 2b. 3 denotes a reboiler. Distillation column A has a diameter of 10 cm and is provided with two packages of Sulzer BX packing having a length of 30 cm. At the top of the column the pressure is 0.5 kPa and the bottom temperature is 113.4° C. Column A is fed with 30 kg/hour of caprolactam with a water content of 0.5 wt. %, 10 parts per million aniline, 10 parts per million USL-1 and 10 parts per million USL-2 and heavy components. Via line 4, 29.5 kg/hour of first bottom product consisting of caprolactam and heavy components is fed to a non-drawn separation device for the separation of the caprolactam and the heavy components. This first bottom product further contains:

<1 parts per million aniline (aniline has a boiling point of 184.4° C. at 100 kPa, as a result of which it is a light component that can easily be separated from caprolactam by distillation)
1 parts per million USL-1
5 parts per million USL-2

A first overhead product from column A is sent via line 5 to the condensation device 2a and subsequently to 2b. Condenser 2a is maintained at 70° C. and condenser 2b at 20° C. The vapour that is not condensed in condenser 2a partly does condense in condenser 2b. The entire condensation device is controlled so that the first overhead product is separated into a first part, which is discharged as water vapour to the vacuum via line 6, and a second part, which, as a combined condensate stream from lines 11 and 9 from condensation stages 2a and 2b, respectively, is fed to a second vacuum distillation column B via line 7 and a non-drawn intermediate storage. A reflux stream of 5 kg/hour from condenser 2a flows via lines 8 and 10 back to column A. The condensate stream in line 7 has a flow rate of 0.35 kg/hour and has the following composition:

98.5 wt. % caprolactam (corresponding to 1.1% of the caprolactam fed to the first vacuum distillation)
1.4 wt. % water
450 parts per million aniline
211 parts per million USL-1
190 parts per million USL2

This condensate stream in line 7 is discontinuously, as said via a non-drawn intermediate storage, fed at a rate of 1000 g/hour to a second vacuum distillation column B with a diameter of 5 cm and provided with two packages of Sulzer BX packing each having a length of 100 cm. At the top of this column the applied pressure is 3 kPa and the bottom temperature is 161.0° C. Condenser 12 is cooled at 70° C. In column B the condensate stream from line 7 is separated into a second overhead product and a second bottom product.

The second overhead product, consisting of water and light components, is passed via line 13 to the condensation device 12 where it is separated into a part containing mainly water, which is discharged as vapour phase to the vacuum via line 14, and a part containing mainly light components, which partly flows back into column B as reflux at a flow rate of 100 to 150 g/hour via lines 15 and 16, while another part is drained via lines 15 and 17.

At a flow rate of 970 g/hour the second bottom product is subjected, via line 18, to a hydrogenation to be described below and is subsequently incorporated into the main caprolactam stream as for instance entering the first distillation column A via line 1. Reference number 19 denotes a reboiler.

The second bottom product contains less than 1 parts per million aniline, and still 8 parts per million USL-1 and 159 parts per million USL-2 and contains 1.0–1.1% of the caprolactam fed to the first vacuum distillation.

Hydrogenation can take place as follows. In a hydrogenation autoclave a slurry of 500 g of the second bottom product is discontinuously hydrogenated with 50 g water and 100 g RaNi catalyst with stirring for 30 minutes at 90° C. After this, the filtered effluent (hydrogenated second bottom product) contains less than 1 parts per million USL-1 and 20 parts per million USL-2.

The process described above can also be carried out continuously.

This example shows that omitting the recycling of the hydrogenated second bottom product (and the same purity of the first bottom product is to be obtained) would result in a caprolactam loss of 1.1% of the caprolactam fed to the first vacuum distillation.

Comparative Example

Water-containing caprolactam of a composition such as in the preceding Example is purified in the conventional manner in a single column with full overhead water removal via line 20 to the vacuum, see FIG. 2. 15 kg/hour of caprolactam to be purified is fed via line 21 to a vacuum distillation consisting of a column C with a diameter of 5 cm provided with two packages of SulzerBX packing, each having a length of 2 m, use being made of a two-stage condenser 22a and 22b and a reboiler 23, the same as in the Example. The applied pressure at the top of the column is 0,6 kPa and the pressure at the bottom of the column is 2 kPa. The bottom temperature is 143.7° C. The reflux flow rate in line 24 is 4 kg/hour and the bottom product in line 25 has a flow rate of 14.8 kg/hour. The water in line 20 contains 0.05% of the caprolactam fed to the first vacuum distillation.

The bottom product in line 25 here has less than 1 parts per million water, 1 parts per million USL-1 and 9 parts per million USL-2, and is still to be subjected, just like the bottom product in line 4 from the Example (FIG. 1), to a subsequent, non-drawn, processing step for the removal of the heavy components.

By the use of the process according to the invention the first bottom product, in line 4 in the Example, contains 40 parts per million % less unsaturated lactams than the bottom product, in line 25 in the Comparative Example. After analysis this means a reduction in the PAN number by over 1 point.

From the example and the comparative example it is clear that a series arrangement of two distillation columns with a small recycling to a hydrogenation that is usually already present can result in a strong reduction in the factors causing an increase in the pan number while no or substantial no caprolactam is lost.

The invention claimed is:

1. Process for recovering caprolactam from a mixture comprising (i) caprolactam, (ii) water, (iii) light components including unsaturated lactams and (iv) heavy components, wherein the mixture is subjected to a first vacuum distillation resulting in (a) a first bottom product comprising heavy components and part of the caprolactam and in (b) a first overhead product comprising caprolactam, water, and the light components including the unsaturated lactams; and wherein at least part of the unsaturated lactams is subjected to a hydrogenation.

2. Process according to claim 1, wherein the process comprises separating the first overhead product into a first part containing water and light components and a second part containing caprolactam and unsaturated lactams; and hydrogenating said second part.

3. Process according to claim 1, wherein the process comprises separating the first overhead product by subjecting the first overhead product to a second vacuum distillation resulting in a second overhead product comprising water and light components and in a second bottom product comprising caprolactam and unsaturated lactams; and hydrogenating said second bottom product.

4. Process according to claim 1, wherein said hydrogenation results in a hydrogenated mixture, and in that the process further comprises recovering caprolactam from said hydrogenated mixture.

5. Process according to claim 1, wherein said hydrogenation results in a hydrogenated mixture, and in that the process further comprises recycling the hydrogenated mixture to the first vacuum distillation.

6. Process according to claim 1, wherein the mixture is subjected to a hydrogenation in a hydrogenation reactor prior to said first vacuum distillation and in that said hydrogenation of said unsaturated lactams is effected in said hydrogenation reactor.

7. Process according to claim 2, wherein the mixture is subjected to a hydrogenation in a hydrogenation reactor prior to said first vacuum distillation, and in that the process comprises recycling the second part to the hydrogenation reactor.

8. Process according to claim 3, wherein the mixture is subjected to a hydrogenation in a hydrogenation reactor prior to said first vacuum distillation, and in that the process comprises recycling the second bottom product to the hydrogenation reactor.

9. Process according to claim 3, wherein the first vacuum distillation is performed in a first vacuum distillation column and the applied pressure at the top of the first vacuum distillation column is between 0.2 and 3 kPa and the bottom temperature is between 90 and 160° C. and the second vacuum distillation is performed in a second vacuum distillation column and the applied pressure at the top of the second vacuum distillation column is between 1 and 5 kPa and the bottom temperature is between 120 and 170° C.

10. Process according to claim 3, wherein the first overhead product is separated by condensation into a first part containing water and a second part containing caprolactam and light components (including unsaturated lactams), which second part is subjected to the second vacuum distillation.

11. Process according to claim 1, wherein the first bottom product contains more than 90 wt. % of the caprolactam present in the mixture which is fed to the first vacuum distillation.

* * * * *

UNITED STATES PATENT AND TRADEMARK OFFICE
CERTIFICATE OF CORRECTION

PATENT NO. : 7,141,668 B2
APPLICATION NO. : 10/495862
DATED : November 28, 2006
INVENTOR(S) : Smeets et al.

It is certified that error appears in the above-identified patent and that said Letters Patent is hereby corrected as shown below:

IN THE DRAWINGS:

Attached Pages should be included in the corresponding pages of Figures in the patent.

Signed and Sealed this

Twenty-second Day of July, 2008

JON W. DUDAS
*Director of the United States Patent and Trademark Office*

Formula sheet
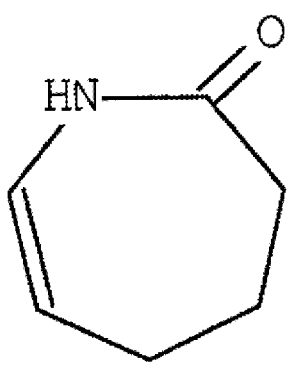
USL-1
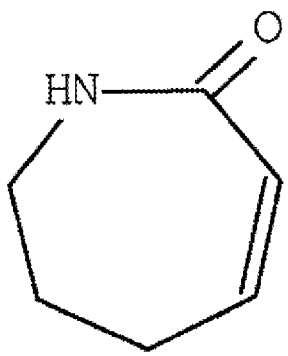
USL-2

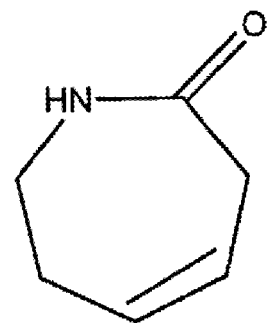
USL-3
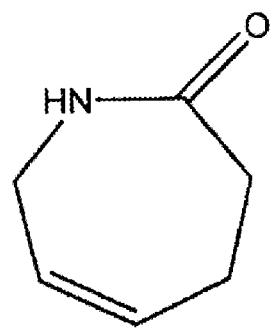
USL-4